United States Patent [19]

Schalke et al.

[11] 4,369,322

[45] Jan. 18, 1983

[54] PROCESS FOR THE PRODUCTION OF SUBSTITUTED ACETONITRILES

[75] Inventors: Peter Schalke; Axel Kleemann, both of Hanau, Fed. Rep. of Germany

[73] Assignee: Degussa AG, Frankfurt, Fed. Rep. of Germany

[21] Appl. No.: 241,836

[22] Filed: Mar. 9, 1981

Related U.S. Application Data

[63] Continuation of Ser. No. 102,933, Dec. 12, 1979, abandoned.

[30] Foreign Application Priority Data

Dec. 15, 1978 [DE] Fed. Rep. of Germany ....... 2854210

[51] Int. Cl.$^3$ ................. C07C 120/00; C07C 121/66; C07C 121/68; C07D 213/57
[52] U.S. Cl. ................. 546/330; 260/465 C; 260/465 F; 260/465 G; 260/465 H; 546/140; 546/141; 546/142; 546/145; 546/153; 546/155; 546/176; 546/177; 546/261; 546/264; 546/284; 546/290; 546/296; 546/303; 549/62; 549/65; 549/74

[58] Field of Search .......... 260/465 C, 465 H, 465 G, 260/465 F; 546/145, 176, 330, 140, 141, 142, 153, 155, 177, 261, 264, 284; 549/74, 62, 65

[56] References Cited

U.S. PATENT DOCUMENTS 2,553,404  5/1951  Dixon .............................. 260/465 C
2,606,917  8/1952  Dixon .............................. 260/465 H
3,936,486  2/1976  Egger et al. .................. 260/465.8 R

OTHER PUBLICATIONS

Grimm et al., Ind. Eng. Chem. Prod. Res. Div., vol. 14, No. 3, (1975), pp. 158-161.

Primary Examiner—Joseph P. Brust
Attorney, Agent, or Firm—Cushman, Darby & Cushman

[57] ABSTRACT

The known synthesis for the production of aromatic substituted acetonitriles by reaction of aromatic substances with cyanogen chloride in the gas phase is improved by feeding the starting materials in gaseous form and separated from each other into the reactor. The process can be used to synthesize in general aromatic and especially hetero-aromatic substituted acetonitrile.

31 Claims, No Drawings

PROCESS FOR THE PRODUCTION OF SUBSTITUTED ACETONITRILES

This is a continuation of application Ser. No. 102,933, filed Dec. 12, 1979, now abandoned.

BACKGROUND OF THE INVENTION

The invention is directed to a process for the production of aromatic or heteroaromatic substituted acetonitriles by the reaction of methyl substituted aromatics or heteroaromatics with cyanogen chloride in the gas phase at elevated temperature. The aromatic or heteroaromatic substituted acetonitriles among other uses are employed as starting materials for the production of medicines and plant protective agents.

It is known to produce aromatic substituted acetonitrile by reaction of methyl substituted aromatics with cyanogen chloride in the gas phase in a reaction tube at a temperature of 500° to 775° C. The starting materials for this are fed in as liquids and vaporized at the entrance of the reactor tube (Grimm, Ind. Eng. Chem., Prod. Res. Div. Vol. 14 (1975) pages 158 to 161. To be sure a favorable transformation is produced in this process but the yield of pure substituted acetonitriles is only moderate. The space-time-yield also is moderate. Besides, decomposition products, particularly carbon black, deposit in the reaction tube, so that the tube after a relatively short operating time is clogged. The process consequently is unusable for use on an industrial scale.

SUMMARY OF THE INVENTION

There has now been found a process for the production of aromatic or heteroaromatic substituted acetonitriles by reaction of methyl substituted aromatic methane or heteroaromatic substituted methane or diaromatic substituted methane or diheteroaromatic substituted methane or aromatic heteroaromatic substituted methane with cyanogen chloride in the gas phase at elevated temperature which is characterized by feeding the aromatic or heteroaromatic compound and cyanogen chloride separately from each other and in gaseous form into the reactor and carrying out the reaction at a temperature between about 550° to 850° C. In this process the yield of pure substituted acetonitriles is substantially higher than in the known process. High space-time-yields are produced. The reactor remains free from deposits over long times of operation. The process is not only usable for the production of aromatic substituted acetonitriles, but is particularly suitable for the production of heteroaromatic substituted acetonitriles. The process is well suited for carrying out the reaction on an industrial scale.

The process of the invention is suited for the production of aromatic or heteroaromatic acetonitriles of the general formula

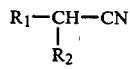   (I)

in which $R_1$ is particularly a hydrogen atom or a phenyl or thiophen group and in which $R_2$ particularly is a phenyl, naphthyl, pyridyl, thiophen, quinolyl or isoquinolyl group which in a given case can have one or more substituents which can be the same or different. These substituents especially can be halogen atoms, preferably fluorine or chlorine atoms, or methyl, hydroxyl or cyano group. Other substituents include aryloxy and methoxy.

To carry out the process cyanogen chloride is reacted with a methyl substituted aromatic or heteroaromatic of the general formula:

$$R_1-CH_2-R_2 \qquad (II)$$

in which $R_1$ and $R_2$ are defined as in formula I. Examples include Toluene, 1,2-Dimethylbenzene, 1,3-Dimethylbenzene, 1,4-Dimethylbenzene, 1,2,3-Trimethylbenzene, 1,3,5-Trimethylbenzene, 1,2,4,5-Tetramethylbenzene, 2-Fluorotoluene, 3-Fluorotoluene, 4-Fluorotoluene, 2-Chlorotoluene, 3-Chlorotoluene, 4-Chlorotoluene, 3-Bromotoluene, 3-Hydroxytoluene, 4-Hydroxytoluene, 2-Cyanotoluene, 3-Cyanotoluene, 4-Cyanotoluene, 2-Fluoro-4-chlorotoluene, 2-Fluoro-5-chlorotoluene, 2-Fluoro-6-chlorotoluene, 4-Fluoro-2-chlorotoluene, 1-Chloro-3,4-dimethylbenzene, 1-Hydroxy-3,4-dimethylbenzene, 1-Hydroxy-2,6-dimethylbenzene, 1-Cyano-2,4-dimethylbenzene, 1-Methylnaphthalene, 2-Methylnaphthalene, 1,4-Dimethylnaphthalene, 2,6-Dimethylnaphthalene, Diphenylmethane, 4-Hydroxydiphenylmethane, 2-Methylpyridine, 3-Methylpyridine, 4-Methylpyridine, 2,6-Dimethylpyridine, 2,4-Dimethylpyridine, 2,3-Dimethylpyridine, 2,3,6-Trimethylpyridine, 2,4,6-Trimethylpyridine, 2-Methyl-5-ethylpyridine, 6-Chloro-2-Methylpyridine, 2-Methylquinoline, 3,5-Dimethylpyridine, 2-Methylthiophene, 3-Methylthiophene, 2,3-Dimethylthiophene, 2,5-Dimethylthiophene, 3,4-Dimethylthiophene, 2-Benzylthiophene, 3-Benzylthiophene, 5-Chloro-2-methylthiophene, 2,2'-Dithienylmethane.

Additional compounds include 3-phenoxytoluene, 2-phenoxytoluene, 4-phenoxytoluene, 2-methoxytoluene, 3-methoxytoluene, 4-methoxytoluene, 6-methylquinoline, 8-methylquinoline, 1-methylisoquinoline, 3-methylisoquinoline, 2,6-dimethylnaphthalene, 2,3-dimethylnaphthalene.

The reaction temperature and proportions of the reacting materials are dependent on each other in a given case and are adjusted in a given case according to the type of materials reacting.

In general the reaction is undertaken at temperatures between about 550° and 850° C., particularly at temperatures between 600° and 750° C. Although the pressure can be selected at random, thus the process can be operated at normal pressure as well at lower or higher pressures, it is generally advantageous not to deviate substantially from normal pressure.

The molar ratio of the methyl substituted aromatic or heteroaromatic to cyanogen chloride can be selected largely at random, both stoichiometrical as well as under and over stoichiometrical being suitable. In general it is advantageous to employ at least about 1 mole of aromatic or heteroaromatic per mole of cyanogen chloride. Preferably there is added per mole of cyanogen chloride 1 to 10 moles, especially 2 to 6 moles, of the aromatic or heteroaromatic.

The process of the invention is carried out continuously with advantage. For this purpose there is suitably used a reactor of the type of a reactor tube, for example a tube bundle reactor.

According to the invention the starting materials, the methyl substituted aromatic or heteroaromatic and the cyanogen chloride are fed into the reactor in gaseous form and separate from each other. The materials therefore in entering the reactor have temperatures which lie above their boiling temperatures. It is advantageous for the most part, to feed the materials into the reactor with temperatures which approach the reaction temperature, thus with temperatures between about 400° and 800° C., particularly between 550° and 700° C.

The reaction mixture can be diluted by inert gases such as nitrogen or steam. These can be supplied together with the aromatic or heteroaromatic to be reacted, and/or with the cyanogen chloride or separately from these materials. It is generally suitable to use not more than 2 parts by volume of inert gas per part by volume of cyanogen chloride. The cyanogen chloride can be added in pure form or as the crude product as it results in the production of cyanogen chloride from chlorine and hydrogen cyanide.

The pure substituted acetonitrile can be recovered from the reaction mixture in various ways, for example through distillation or crystallization. It is advantageous to cool the reaction mixture directly after leaving the reactor to a temperature below 100° C. This can take place in customary manner, particularly through a washing of the gases with liquids, preferably water. Especially in the cases where heteroaromatic substituted acetonitriles are produced it is advantageous to treat the reaction mixture directly with bases, it is suitable to add to the wash liquids basically acting materials. Advantageously alkali hydroxides, alkali carbonates or alkali bicarbonates, e.g., sodium hydroxide, potassium hydroxide, sodium carbonate, potassium carbonate, sodium bicarbonate and potassium bicarbonate.

Unless otherwise indicated all parts and percentages are by weight. The process can comprise, consist essentially of or consisting of the steps set forth and the materials can comprise, consist essentially of or consist of those set forth.

DESCRIPTION OF THE PREFERRED EMBODIMENTS

EXAMPLE 1

As the reactor there was used a quartz tube 1 meter long and 55 mm wide which was heated from the outside. There were fed into the tube separately from each other in homogeneous flow hourly 2 normal liters of nitrogen and 86 grams (1.4 moles) of cyanogen chloride which were preheated to 550° C. and 561 grams (6.1 moles) of toluene which likewise was preheated to 550° C. The reacted temperature was 680° C. The reaction mixture was treated with water in a gas washer directly post-connected to the reactor and cooled to 30° C. The phases in the aqueous mixture which discharged from the gas washer were separated. The organic phase was fractionally distilled. The unreacted toluene was recovered thereby. The yield of phenylacetonitrile amounted to 146 grams hourly, corresponding to 89%, based on the cyanogen chloride added. The phenylacetonitrile had a boiling point of 233° to 234° C. Its purity was over 98%.

EXAMPLE 2

As the reactor there was used a quartz tube 1 meter long and 39 mm wide which has heated from the outside. There were fed into the tube separately from each other in homogeneous flow hourly 37 grams (0.6 mole) of cyanogen chloride which was preheated to 600° C. and 396 grams (2.5 moles) of diphenylmethane which likewise was preheated to 600° C. The reaction temperature was 650° C. The reaction mixture was treated with water in a gas washer directly post-connected to the reactor and cooled to 30° C. The phases in the aqueous mixture which discharged from the gas washer were separated. The organic phase was fractionally distilled. The unreacted diphenylmethane was thereby recovered. The yield of diphenylacetonitrile amount to 83% based on the cyanogen chloride added.

EXAMPLE 3

As the reactor there was used a quartz tube 1 meter long and 20 mm wide which was heated from the outside. There were fed into the tube separately from each other in homogeneous flow hourly 7.1 grams (0.12 mole) of cyanogen chloride and 42.8 grams (0.46 mole) of 3-methylpyridine) both of which were preheated to 550° C. The reaction temperature was 680° C. The reaction mixture was treated hourly with 1.2 liters of 5 percent aqueous sodium hydroxide solution in a gas washer directly post-connected to the reactor. The aqueous mixture which discharged from the gas washer was extracted hourly with 2 liters of dichloromethane. By distillation of the organic phase there were recovered the dichloromethane and the unreacted 3-methylpyridine. The pyridine-3-acetonitrile obtained had a boiling point of 101° to 109° C. at 1, 5 mbar. Its purity was 98 to 99%. The yield amounted to 10.4 grams, corresponding to 75% based on the cyanogen chloride added.

EXAMPLE 4

As the reactor there was used a quartz tube 1 meter long and 39 mm wide which was heated from the outside. There were fed into the tube separately from each other in homogeneous flow hourly 37 grams (0.6 mole) of cyanogen chloride and 265 grams (2.7 moles) of 3-methylthiophene, both of which were preheated to 580° C. The reaction temperature was 680° C. The reaction mixture was condensed by cooling to 30° C. in a directly post-connected receiver. The condensate was fractionally distilled. The unreacted 3-methylthiophene was recovered thereby. The thiophene-3-acetonitrile had a boiling point of 78° to 83° C. at 2 mbar. Its purity as determined by gas chromatography was over 98%. The yield was 77% based on the cyanogen chloride added.

EXAMPLES 5 TO 29

Examples 5 to 29 are set forth in Table 1. In each case the procedure of Example 2 was followed but the cyanogen chloride was reacted with the compounds which are set forth as starting materials. Under mole ratio there is given how many moles of the starting material were added per mole of cyanogen chloride. The temperature is the reaction temperature in 6° C. The yield is based on the cyanogen chloride added and stated in weight percent.

EXAMPLES 30 TO 39

Examples 30 to 39 are set forth in Table 2. The procedure was the same as in Example 3 in each case. For the rest see the explanations of Table 1 for Example 5 to 29.

EXAMPLES 40 TO 44

Examples 40 to 44 are set forth in Table 3. The procedure was the same as in Example 4 in each case. For the rest see the explanations of Table 1 for Examples 5 to 29.

TABLE 1

| No. | Starting Material | Molar Ratio | Temperature | Product | Yield |
|---|---|---|---|---|---|
| 5 | 2-Fluorotoluene | 5.7 | 740 | 2-Fluorophenylacetonitrile | 77 |
| 6 | 3-Fluorotoluene | 5.2 | 740 | 3-Fluorophenylacetonitrile | 89 |
| 7 | 4-Fluorotoluene | 4.6 | 700 | 4-Fluorophenylacetonitrile | 75 |
| 8 | 2-Chlorotoluene | 5.0 | 725 | 2-Chlorophenylacetonitrile | 70 |
| 9 | 3-Chlorotoluene | 5.0 | 715 | 3-Chlorophenylacetonitrile | 75 |
| 10 | 4-Chlorotoluene | 4.0 | 670 | 4-Chlorophenylacetonitrile | 60 |
| 11 | 3-Bromotoluene | 3.5 | 705 | 3-Bromophenylacetonitrile | 61 |
| 12 | 3-Hydroxytoluene | 5.0 | 720 | 3-Hydroxyphenylacetonitrile | 29 |
| 13 | 4-Hydroxytoluene | 4.4 | 670 | 4-Hydroxyphenylacetonitrile | 52 |
| 14 | 2-Cyanotoluene | 4.2 | 710 | 2-Cyanophenylacetonitrile | 67 |
| 15 | 3-Cyanotoluene | 4.8 | 750 | 3-Cyanophenylacetonitrile | 88 |
| 16 | 4-Cyanotoluene | 4.7 | 760 | 4-Cyanophenylacetonitrile | 75 |
| 17 | 2-Fluoro-4-chlorotoluene | 4.6 | 720 | 2-Fluoro-4-chlorophenylacetonitrile | 76 |
| 18 | 2-Fluoro-5-chlorotoluene | 4.1 | 720 | 2-Fluoro-5-chlorophenylacetonitrile | 89 |
| 19 | 2-Fluoro-6-chlorotoluene | 4.5 | 740 | 2-Fluoro-6-chlorophenylacetonitrile | 89 |
| 20 | 4-Fluoro-2-chlorotoluene | 4.3 | 720 | 4-Fluoro-2-chlorophenylacetonitrile | 79 |
| 21 | 1,2-Dimethylbenzene | 4.4 | 680 | 2-Methylphenylacetonitrile | 89 |
| 22 | 1,3-Dimethylbenzene | 4.6 | 700 | 3-Methylphenylacetonitrile | 95 |
| 23 | 1,4-Dimethylbenzene | 4.1 | 670 | 4-Methylphenylacetonitrile | 77 |
| 24 | 1-Chloro-3,4-dimethylbenzene | 4.0 | 670 | 3-Chloro-6-methylphenylacetonitrile | 56 |
| 25 | 1,3,5-Trimethylbenzene | 4.3 | 670 | 3,5-Dimethylphenylacetonitrile | 79 |
| 26 | 1-Methylnaphthalene | 3,7 | 650 | Naphthyl-1-acetonitrile | 62 |
| 27 | 1,2,4,5-Tetramethylbenzene | 3.8 | 620 | 2,4,5-Trimethylphenylacetonitrile | 73 |
| 28 | 3-Phenoxytoluene | 4.1 | 670 | 3-Phenoxyphenylacetonitrile | 48 |
| 29 | 2,4-Dichlorotoluene | 4.8 | 705 | 2,4-Dichlorophenylacetonitrile | 63 |

TABLE 2

| No. | Starting Material | Molar Ratio | Temperature | Product | Yield |
|---|---|---|---|---|---|
| 30 | 2-Methylpyridine | 5.0 | 680 | Pyridin-2-acetonitrile | 76 |
| 31 | 3-Methylpyridine | 4.1 | 690 | Pyridin-3-acetonitrile | 77 |
| 32 | 4-Methylpyridine | 4.3 | 710 | Pyridin-4-acetonitrile | 65 |
| 33 | 2,6-Dimethylpyridine | 5.9 | 630 | 6-Methylpyridin-2-acetonitrile | 81 |
| 34 | 2,4-Dimethylpyridine | 4.9 | 640 | 4-Methylpyridin-2-acetonitrile | 74 |
| 35 | 2,4,6-Trimethylpyridine | 5.5 | 625 | 4,6-Dimethylpyridin-2-acetonitrile | 85 |
| 36 | 2,3-Dimethylpyridine | 5.1 | 650 | 3-Methylpyridin-2-acetonitrile | 88 |
| 37 | 3,5-Dimethylpyridine | 4.8 | 670 | 5-Methylpyridin-3-acetonitrile | 51 |
| 38 | 2-Methyl-6-chloropyridine | 5.1 | 660 | 6-Chloropyridin-2-acetonitrile | 20 |
| 39 | 2-Methyl-5-ethylpyridine | 4.8 | 680 | 5-Ethylpyridin-2-acetonitrile | 38 |

TABLE 3

| No. | Starting Material | Molar Ratio | Temperature | Product | Yield |
|---|---|---|---|---|---|
| 40 | 2-Methylthiophene | 5.1 | 660 | Thiophene-2-acetonitrile | 67 |
| 41 | 3-Methylthiophene | 4.5 | 680 | Thiophene-3-acetonitrile | 77 |
| 42 | 2,5-Dimethylthiophene | 5.3 | 650 | 5-Methylthiophene-2-acetonitrile | 90 |
| 43 | 2,3-Dimethylthiophene | 4.9 | 670 | 2-Methylthiophene-3-acetonitrile and 3-Methylthiophene-2-acetonitrile | (each) (41) |
| 44 | 2-Benzylthiophene | 3.7 | 660 | 2-Thiopheneacetonitrile-α-phenyl | 56 |

What is claimed is:

1. A process for the production of an aromatic or heteroaromatic substituted acetonitrile of the formula

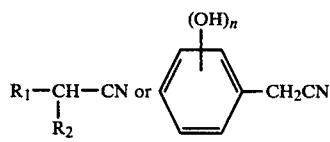

where $R_1$ is hydrogen, phenyl, thienyl, pyridyl, quinolyl or isoquinolyl and $R_2$ is thienyl, pyridyl, quinolyl or isoquinolyl or $R_2$ is a substituted thienyl, pyridyl, quinolyl or isoquinolyl group having at least one substituent wherein the substituent is lower alkyl, halogen, hydroxy, cyano, phenoxy or methoxy and n is 0 or 1 comprising reacting a substituted methane of the formula $R_1$—$CH_2$—$R_2$, toluene or hydroxytoluene with cyanogen chloride in the gas phase by feeding the substituted methane and cyanogen chloride separately from each other and in gaseous form into the reactor at a temperature close to the reaction temperature and carrying out the reaction at a temperature between 550° and 850° C., cooling the reaction mixture immediately after leaving the reactor to a temperature below 100° C. and treating the reaction mixture with an aqueous base.

2. A process according to claim 1 wherein there are employed 1 to 10 moles of the substituted methane of the formula $R_1$—$CH_2$—$R_2$, toluene or hydroxytoluene per mole of cyanogen chloride.

3. A process according to claim 1 wherein there is employed at least about one mole of the substituted methane of the formula $R_1$—$CH_2$—$R_2$, toluene or hydroxytoluene per mole of cyanogen chloride.

4. A process according to claim 3 wherein there are employed 1 to 10 moles of the substituted methane of the formula $R_1$—$CH_2$—$R_2$, toluene or hydroxytoluene per mole of cyanogen chloride.

5. A process according to claim 4 wherein there are employed 2 to 6 moles of the substituted methane of the formula $R_1$—$CH_2$—$R_2$, toluene or hydroxytoluene per mole of cyanogen chloride.

6. A process according to claim 1 wherein the substituted acetonitrile formed has the formula $$R_1-\underset{\underset{R_2}{|}}{CH}-CN$$

7. A process according to claim 1 wherein the substituted acetonitrile formed is phenylacetonitrile.

8. A process according to claim 1 wherein the substituted acetonitrile formed is hydroxyphenylacetonitrile.

9. A process according to claim 6 wherein there is employed as the substituted methane mono methyl pyridine.

10. A process according to claim 9 wherein the the methyl pyridine is 3-methyl pyridine.

11. A process according to claim 9 wherein the methyl pyridine is 2-methyl pyridine.

12. A process according to claim 6 wherein there is employed as the substituted methane 2-benzylthiophene.

13. A process according to claim 8 wherein there is employed as the substituted methane 4-hydroxytoluene.

14. A process according to claim 1 wherein the substituted methane, toluene or hydroxytoluene and cyanogen chloride are supplied to the reactor at a temperature of about 400° to 800° C.

15. A process according to claim 14 which employs $R_1-CH_2-R_2$ wherein $R_1$ is hydrogen and $R_2$ is methyl pyridyl having 0 to 2 additional methyl groups, 0 to 1 ethyl group and 0 to 1 halogen, the total number of substituents on the pyridine ring being 1 to 3.

16. A process according to claim 15 wherein $R_2$ is pyridyl having 0 to 2 methyl groups and 0 to 1 ethyl group, the total number of substituents on the pyridine ring being 1 to 3.

17. A process according to claim 14 wherein $R_1$ is hydrogen and $R_2$ is methylthienyl having 0 to 1 additional methyl group attached to the ring.

18. A process according to claim 14 wherein there is employed benzyl thiophene.

19. A process according to claim 14 wherein there is employed 4-hydroxytoluene.

20. A process according to claim 14 wherein the substituted methane, toluene or hydroxytoluene and cyanogen chloride are supplied to the reactor at a temperature of about 550° to 700° C.

21. A process according to claim 20 wherein there is employed methylthiophen having 0 to 1 additional methyl group attached to the ring.

22. A process according to claim 20 wherein there is employed benzyl thiophene.

23. A process according to claim 20 wherein there is employed 4-hydroxytoluene.

24. A process according to claim 20 wherein there is employed methyl pyridine having 0 to 2 additional methyl groups, 0 to 1 ethyl group and 0 to 1 halogen, the total number of substituents on the pyridine ring being 1 to 3.

25. A process according to claim 6 wherein $R_2$ is pyridyl having 0 to 2 methyl groups, 0 to 1 ethyl group and 0 to 1 halogen, the total number of substituents on the pyridine ring being 1 to 3.

26. A process according to claim 25 wherein $R_2$ is pyridyl having 0 to 2 methyl groups and 0 to 1 ethyl group, the total number of substituents on the pyridine ring being 1 to 3.

27. A process according to claim 6 wherein $R_2$ is thienyl having 0 to 1 methyl group attached to the ring.

28. A process according to claim 6 wherein $R_1$ is phenyl, thienyl, pyridyl, quinolyl or isoquinolyl and $R_2$ is thienyl, pyridyl, quinolyl or isoquinolyl.

29. A process according to claim 28 wherein $R_1$ is phenyl, thienyl or pyridyl and $R_2$ is thienyl or pyridyl.

30. A process according to claim 28 where $R_1$ is phenyl and $R_2$ is thienyl.

31. A process according to claim 1 wherein $R_1$ is hydrogen and $R_2$ is thienyl, pyridyl, quinolyl, or isoquinolyl and in addition has 0 to 2 additional substituents selected from the group consisting of lower alkyl, hydroxy, cyano, halogen, and phenoxy.

* * * * *